United States Patent [19]

Esty

[11] 4,014,343
[45] Mar. 29, 1977

[54] DETACHABLE CHUCK FOR ELECTRO-SURGICAL INSTRUMENT

[75] Inventor: Janet M. Esty, Boulder, Colo.

[73] Assignee: Neomed Incorporated, Boulder, Colo.

[22] Filed: Apr. 25, 1975

[21] Appl. No.: 571,517

[52] U.S. Cl. .................... 128/303.14; 128/303.17; 219/233; 219/234; 339/31 T; 339/108 TP

[51] Int. Cl.$^2$ .................... A61B 17/40; A61N 3/06

[58] Field of Search ................ 128/303.13, 303.14, 128/303.17, 303.18, 303.1, 404–409; 219/227, 229, 230, 233, 238, 234; 228/55; 339/31 T, 108 TP

[56] References Cited

UNITED STATES PATENTS

| | | | |
|---|---|---|---|
| 1,814,791 | 7/1931 | Ende | 128/303.17 |
| 2,293,455 | 8/1942 | Disch et al. | 219/230 |
| 3,048,687 | 8/1962 | Knowles | 219/230 |
| 3,494,363 | 2/1970 | Jackson | 128/303.17 |
| 3,799,168 | 3/1974 | Peters | 128/303.14 |
| 3,801,766 | 4/1974 | Morrison | 128/303.14 |
| 3,807,404 | 4/1974 | Weissman et al. | 128/303.14 |
| 3,825,004 | 7/1974 | Durden | 128/303.17 |
| 3,847,153 | 11/1974 | Weissman | 128/303.14 |

Primary Examiner—Robert W. Michell
Assistant Examiner—Lee S. Cohen
Attorney, Agent, or Firm—John E. Reilly

[57] ABSTRACT

A generally flat insulator chuck is arranged to retain surgical electrodes so that the working area of the electrodes extends externally on one end and an electrical circuit accomodating prong is contained within a recessed chamber at the other end. The recessed chamber is dimensioned so as to effect continuous contouring relative to a receiving control handle apparatus in such a manner that the physical stress is translated between the insulator sidewalls of the chuck and the insulator of an extended plug on the handle. The electrical connection extension prong within the recess slidingly engages an electrical connector embedded within the handle extension so as to provide electrical contact free of physical stress from usage. Locking and guiding arrangements cooperate between the handle and the chuck to further insure firm attachment.

7 Claims, 7 Drawing Figures

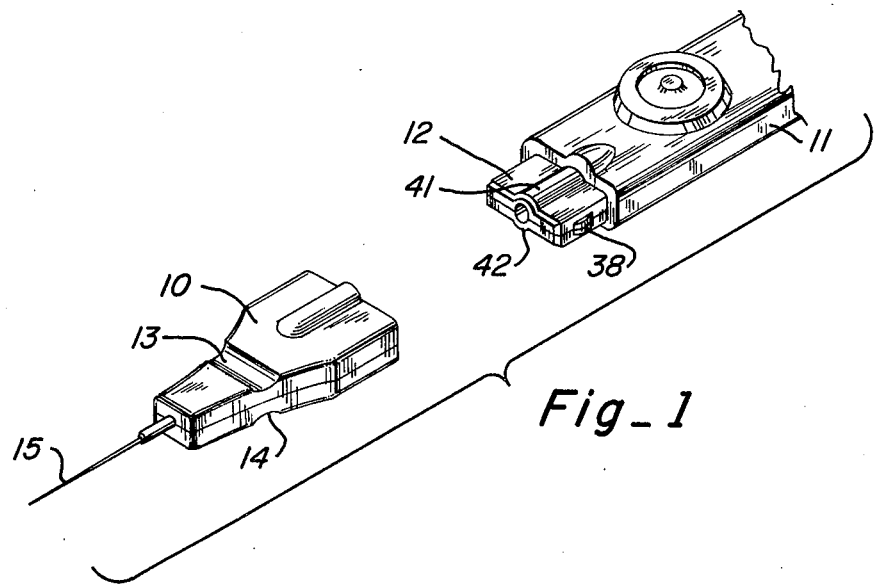
Fig_1
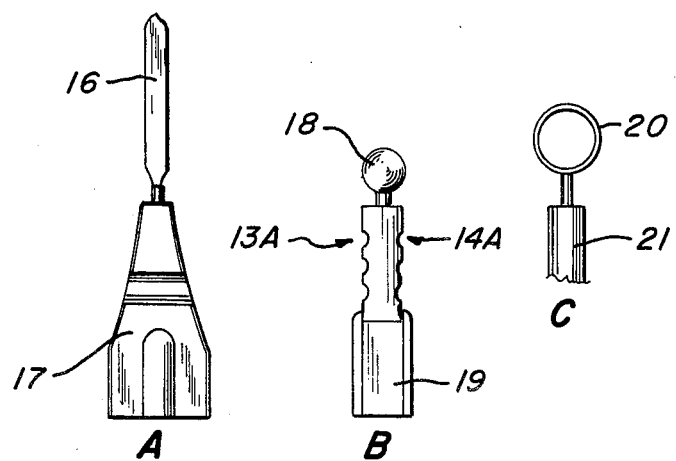
Fig_2
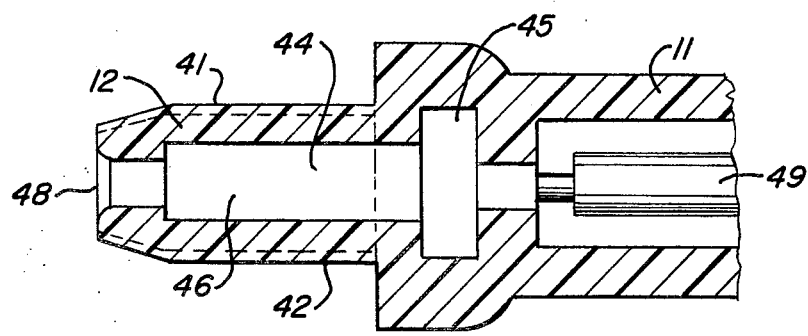
Fig_3

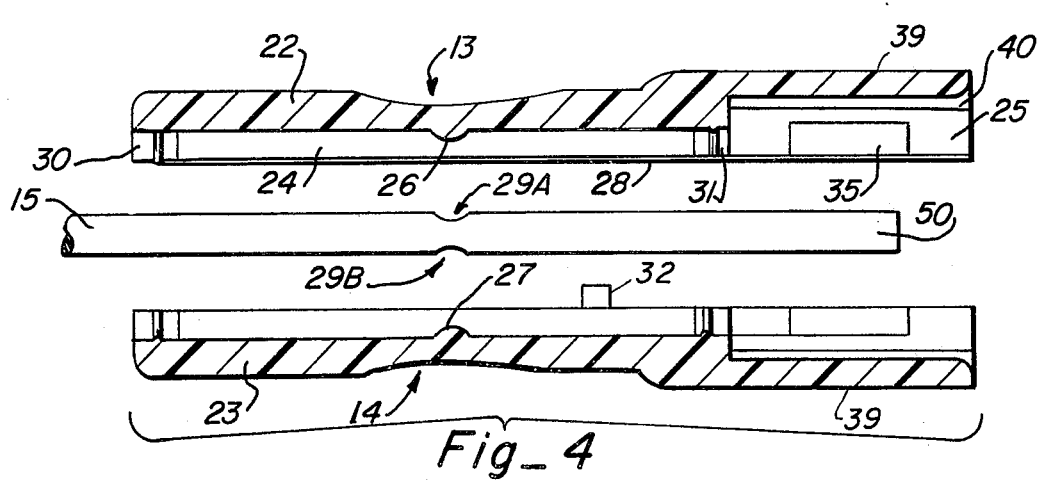
Fig_4
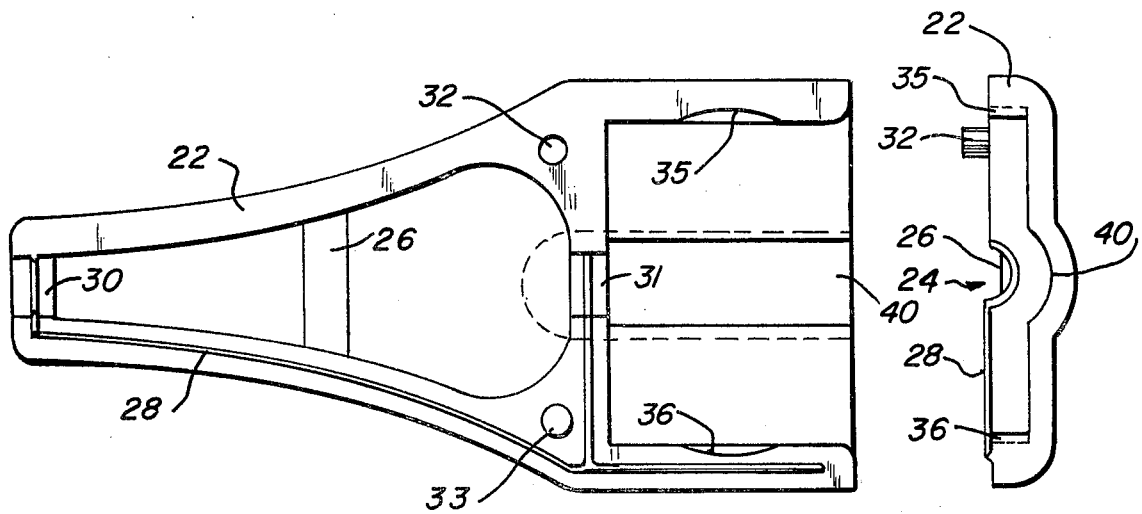
Fig_5
Fig_6
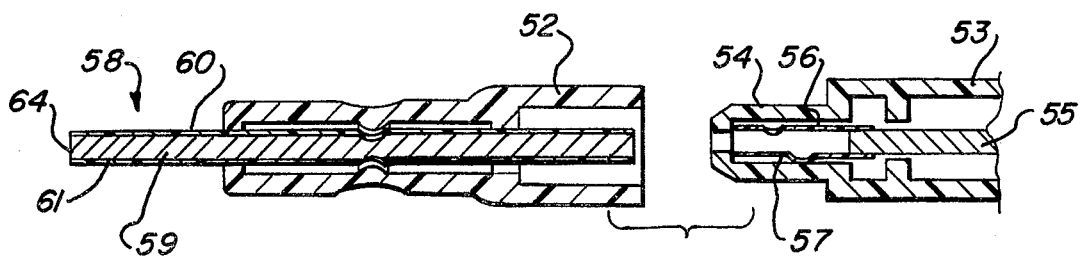
Fig_7

DETACHABLE CHUCK FOR ELECTRO-SURGICAL INSTRUMENT

CROSS REFERENCE TO RELATED APPLICATION

The detachable electro-surgical chuck described in this application is particularly well-suited for use in conjunction with structure shown in the concurrently filed application entitled IMPROVED ELECTRO-SURGICAL INSTRUMENT by J.M. Esty and C.E. Taylor Ser. No. 571,508, which is assigned to the same assignee as this application.

BACKGROUND OF THE INVENTION

The present invention relates to apparatus for removably attaching electro-surgical electrodes to apparatus which interfaces with electro-surgical signal generators. More particularly, the present invention relates to electrosurgical electrode retaining chucks for interfacing with a retaining handle so that the electrode can be used passively for some purposes and/or for electro-surgical procedures.

The development of electro-surgical signal generators for providing various functions to the surgeon has been followed with development of apparatus which can establish a manual interface between these signal generators and the electrode as is described in detail in the copending application entitled Improved Electro-Surgical Instrument by Esty and Taylor. Further, it has been desirable in many circumstances to have the electrode useful for passive surgical procedures as well as to be available for electro-surgical functions. It has also been recognized that different surgical tools are required for many surgical procedures and thus there is a need for a common interface handle and an arrangement for replacing the particular electrode attached to that handle as the need dictates.

A typical prior art arrangement is to provide a recess at the end of a cylindrical holder with the electrode merely being force-fit into that slot. An arrangement for providing such a function is shown incidentally in copending application by J. W. Jarrard entitled Switching Device for Electro-Surgical Instruments, Ser. No. 315,678, filed Dec. 15, 1972, now U.S. Pat. No. 3,911,241 and assigned to the same assignee as this application. Another arrangement with a slotted retaining collar is generally shown in U.S. Pat. No. 3,746,814 by Lackey, et al. Yet another arrangement for providing a replaceable electrode through a threaded cap is shown in U.S. Pat. No. 3,648,001 by Anderson, et al. Such devices suffer from several disadvantages. For instance, stresses from usage of the electrode are transferred directly to the electrical contact at the retaining handle thus tending to degrade the electrical connection over a period of time. Further, they do not provide adequate support against unintended rotation of the electrode during usage particularly after use in many electro-surgical procedures. Still further, the insulation around the base of the electrode frequently becomes weakened from usage thereby exposing the user to burns when the handle must be gripped near the electrode and also hazards burns at the wound edge. Another disadvantage is that the electrodes are difficult to pick up and insert or remove from the handle especially when surgical gloves are being worn. In addition, the opening at the end of the handle where the electrode is inserted is exposed to seepage thereinto be contaminants such as blood during use which can disrupt the handle's electrical functions and also cause sterilization problems.

SUMMARY OF THE INVENTION

The present invention is directed to an electro-surgical electrode retaining chuck which is adapted for removable attachment to a generally elongated interfacing handle, such as, that shown in the copending application entitled Improved Electro-Surgical Instrument by Esty and Taylor. More particularly, the electro-surgical electrode chuck of this invention is of a somewhat flattened cup-shaped configuration and is adapted to retain an electrode therein so that one end of the electrode is externally exposed for surgical procedure usage when the other end is extended into a recessed chamber of the insulator material forming the chuck housing. This recessed chamber has a generally rectangular cross section and is of sufficient depth to cooperate with the connecting probe on the attachment handle so that the exposed electrode within the chamber will slidingly engage the receiving connector in the handle while any lateral physical stresses from use of the device will be transposed into the supporting insulating material without disturbing the electrical connection. Additionally, this physical supporting arrangement prevents any unintended rotation of the electrodes when attached to the handle for use in a surgical procedure. A locking arrangement is preferably incorporated in the device for a snap-on type of retention and guiding means can be included to insure proper alignment of the electrical connectors. The resultant device effectively forms a continuous, substantially flat contour with the interfacing handle so that the surgical feel associated with scalpels and the like is retained. Further, the chuck is easily detachable for cleaning or sterilization purposes and effectively provides an electrically insulated environment as well as an isolation configuration for the electrodes so that seepage contamination and inadvertent burning problems are significantly ameliorated. The chuck configuration also makes it easy to grip for usage or for attachment and removal relative to the handle.

An object of this invention is to provide a novel and improved apparatus for retaining surgical electrodes so that they can be removably attached to an electro-surgical generator interfacing handle.

A further object of this invention is to provide an electro-surgical electrode retaining chuck which establishes a reliable electrical interconnection while removing stresses from that connection during usage.

A further object of this invention is to provide an electro-surgical electrode chuck which environmentally isolates the electrical connection from the electrode retained in the chuck while providing a positive and firm attachment of the chuck to an interfacing handle.

The foregoing and other objects, features and advantages of the present invention will be more apparent in view of the following detailed description of an exemplary preferred embodiment.

BRIEF DESCRIPTION OF THE DRAWINGS

FIG. 1 is a perspective view showing the interrelationship of an electro-surgical electrode retaining chuck relative to the attaching probe of an interfacing handle.

FIG. 2 illustrates three exemplary arrangements of electrode tips which can be included in chucks in accordance with this invention.

FIG. 3 is a side partially sectioned view of the attaching probe associated with the interfacing handle.

FIG. 4 is an exploded sectional view of the chuck housing showing its interrelationship with the end of an electro-surgical electrode.

FIG. 5 is a bottom view of the upper housing shown in FIG. 4.

FIG. 6 is an end rear view of the housing section shown in FIGS. 4 and 5; and

FIG. 7 is a side section view of a bipolar electrode showing its interrelation with a receiving housing.

DETAILED DESCRIPTION OF THE PREFERRED EMBODIMENTS

FIG. 1 shows the interrelationship between detachable chuck 10 and an interfacing handle 11. The portion of handle 11 pertinent to the replaceable chuck is shown, the remaining detail and interrelationships of the elements in handle 11 being otherwise immaterial to this invention. However, the apparatus contained within housing 11 is described in considerably greater detail in copending application entitled Improved Electro-Surgical Instrument by Esty and Taylor. As described in that application, the body of interfacing instrument 11 is substantially flat so as to provide the general feel of a passive surgical instrument but can include switching apparatus for selecting electro-surgical procedures as desired. An extension probe 12 at one end of body 11 has reduced dimensions and is adapted to be inserted into a complementary socket or recess in the end of; chuck 10 so that the total assembly has continuous substantially flat passive instrument-like dimensions. Chuck 10 includes two transversely extending, upper and lower external grooves 13 and 14 on opposite surfaces thereof. Grooves 13 and 14 are relatively shallow to enhance gripping of the chuck 10 for attachment or removal from probe 12 of handle 11.

Chuck 10 of FIG. 1 is shown by way of example as retaining a needle point electro-surgical electrode 15. However, it will be readily recognized that a detachable electro-surgical electrode chuck in accordance with the present invention can include any of the wide variety of surgically useful exposed portions. For instance, FIG. 2A shows a knife blade or scalpel type of electrode 16 which is retained within a replaceable chuck housing 17. Thus the blade 16 can be used for some passive surgical procedures although its primary utility is for electro-surgical functions. Further, FIG. 2B shows a ball 18 retained within chuck 19 such as might be particularly useful for selected cauterizing operations or the like. FIG. 2B also illustrates a potential modification of the grip enhancing transverse grooves in the form of serrated grooves 13A and 14A. FIG. 2C illustrates a closed loop wire arrangement 20 retained within chuck 21. As is well known, high frequency or RF electro-surgical signals introduced to a loop configuration can be used for surgically cutting tissue. The aforementioned examples of exposed electrode configurations for electro-surgical applications are all so-called unipolar in that the electrical circuit is actually completed by an electrical circuit return path attachment to the patient so that a single conductor passes through the chuck housing. However, it will be readily recognized that the present invention is not restricted to a single electro-surgical electrode but can support a multiplicity of such electrodes. For instance, bipolar contacts wherein a pair of electrodes are passed through the chuck housing and into a pair of receiving connectors in the housing frame of the handle can also be provided and thus not require separate return path. One example is shown in FIG. 7 which will be described later.

FIG. 4 is an exploded view of the electrode retaining chuck 10 of this invention. Preferably chuck 10 is fabricated from two identical casing halves or sections such as upper housing 22 and lower housing 23 so as to be of flat generally rectangular configuration Casings 22 and 23 are preferably molded from polycarbonate plastics such as Merlon M-50, Lexan 2014 or equivalent. Each of these casings is formed with an interior lateral channel 24 and a posterior chamber or end socket 25 into which electrode 15 partially extends. Electrode 15 is retained by transversely extending nubs 26 and 27 which fit into transverse slots 29A and 29B across the top and bottom of electrode 15. The casings are preferably sonically welded after electrode 15 is located therein. Although FIG. 5 illustrates the underside of the upper casing 22, the lower casing 23 is correspondingly formed other than for the exceptions hereinafter noted. Thus, as seen in FIG. 5, opposite sides of each casing half converge forwardly from the straight parallel sidewalls on opposite sides of the chamber 25. In addition, a raised head 28 extends around one side of the lower surface of casing 22 and the opposite side of the upper surface of casing 23 as well as around the periphery of collars 30 and 31. Further, a pin 32 is molded to profect from one side of each casing for insertion into a matching socket 33 which is molded into the confronting surface of the other casing to facilitate alignment and interconnection of the casings. Accordingly, after appropriately locating electrode 15 within the channel 24 of each casing 22 and 23 via ridges 26 and 27 and slots 29, sonic welding along the contacting surfaces of the casings will effect bonding between those two casings, and bonding between the ridges 26 and 27 and slots 29 as well as the collars 30 and 31 will also effect a complete bonding peripherally around the electrode so as to completely seal it within the interior of the casing assembly.

Notches 35 and 36 on opposite sides of the chamber 25 of both casings 22 and 23 provide a detent for receiving locking tabs, such as, is shown at 38 on opposite sides of the probe 12 in FIG. 1. Still further, a longitudinally extending groove such as 40 is formed to extend centrally along the inner surface of each substantially flat wall 39 above and below the chamber 25 so as to accomodate alignment ridges 41 and 42 on the probe 12 in attaching the chuck 10 to housing 11.

An exemplary mating extension probe 12 of the interface handle 11 is shown in section in FIG. 3. An electrical connector in the form of a sleeve 44 with an enlarged base collar 45 is retained within housing 11 by a tubular section 46 which typically may be a longitudinally split arrangement, and the ends of the connector 44 in opening or bore 48 are somewhat outwardly flared and generally spring-biased in closing relation. This connector 44 is electrically attached to wire 49 which extends through the length of handle housing 11 to ultimate connection at the electro-surgical generator as is described in the aforementioned copending application entitled Improved Electro-Surgical Instrument.

After a chuck has been assembled as has been described hereinbefore for FIGS. 4, 5 and 6, the transverse ridges 13 and 14 facilitate gripping of this chuck and the arcuate guiding ridges 41 and 42 of probe 12 mate with the internal axial grooves 40 of chuck 10 so as to provide alignment as the probe is inserted until tabs 38 have snap-locked into engagement with internal notches 35 and 36 within the inner chamber 25. Further, a shank or cylindrical end 50 of electrode 15 which protrudes into chamber 25 will enter the bore 48 of probe 12 and slide against tubular section 46 of connector 44 so as to insure electrical contact. The split, spring-biased arrangement of tubular section 46 can further augment this wiping action. In any event, complete assembly of the chuck onto the receiving probe 12 results in a configuration which is relatively continuous in contour with handle 11 and also rigidly attached so that transverse forces between chuck 10 and handle 11 are substantially carried by the casings 22 and 23 and housing 11 and not translated to the electrical connection. The generally flat attachment configuration thereby prevents any unintended rotation of the electrode while in use. For electrodes such as 16 and 20 shown in FIGS. 2A and 2C, respectively, such inadvertent rotation is obviously highly undesirable but has been a hazard associated with prior art devices. Still further, the encasing arrangement which results wherein chuch 10 surrounds the probe 12 provides isolation of opening or bore 48 from the environment of potential contamination migration. The complete sealing of chuck 10 around electrode 15 means that it can be easily detached and replaced with other chucks during the operating procedures and also be easily removed for thorough cleaning and sterilization. This enclosing action of chuck 10 relative to probe 12 further insures the integrity of sterilization of that element. A further advantage of this arrangement is that the electrical connection between the electrodes such as 15 and internal connectors 44 are thoroughly insulated from the hand of the operator and likewise from the edge of sides of any wound involved in the surgical procedure. The environmental isolation of the electrode handle interface represents a particularly important advantage of this invention since the liquids associated with surgical operations such as blood are frequently good electrical conductors. Their introduction or migration into handle 11 can result in disruption of the intended electrical function therein as well as producing a conductive path to the outside of housing 11 thereby hazarding burns to the surgeon.

FIG. 7 depicts one arrangement for adapting the present invention for bipolar electrode applications. The chuck housing 52 in this example is preferably fabricated similar to the chuck described above for FIGS. 4–6. Receiving handle 53 has an extension probe portion 54 and a circuit board 55 is mounted within handle 53. Two electrical contacts 56 and 57 are attached to the end of board 55 so as to extend forwardly into probe 54. Contacts 56 and 57 can be leaf-type connectors preferably spring-biased to assure wiping contact when electrode 58 is inserted therebetween. Electrode 58 is preferably composed of an insulating inner core 59 which has conductor strips 60 and 61 extending along opposite sides thereof. Thus an electro-surgical procedure can be performed such as across end face 64 of electrode 58 without requiring a circuit return path through the patient. Contacts 60 and 61 through their connection into connectors 56 and 57, respectively, in handle 53 provide the necessary circuit connections. Note that connectors 56 and 57 typically are attached to conductors or circuit board 55 which are in turn coupled to an electrosurgical generator. It will also be recognized that the apparatus can easily be modified to accommodate two or more separate electrodes through the chuck housing which would connect with matching connectors within the handle housing probe.

Although the exemplary preferred embodiments of this invention have been described with particularity, various applications, changes, modifications and additions relative to the present invention will be readily apparent to those having normal skill in the art without departing from the spirit of this invention.

What is claimed is:

1. A detachable chuck adapted for removable attachment to a substantially flat elongated electrically insulating handle, the handle having a main body with a probe of reduced width and thickness relative to the main body at one end thereof, an electro-surgical signal generator connected to the other end of the handle and a receiving electrical connector contained within the probe extending from the said one end of the handle with the probe being of the same substantially flat configuration as the main body of the handle, said chuck comprising:

a housing of electrically insulating material having external dimensions conforming to the external dimensions of the handle main body and having a chamber opening into one end with the internal dimensions of said chamber conforming to the external dimensions of the handle probe for frictional engagement therebetween, an elongated electrical conductor having an electrosurgical electrode on one end and a shank on the other end, said conductor being permanently and sealably retained by said housing so that said shank extends at least partially into said housing chamber while said electro-surgical electrode extends externally from said housing on the end opposite said chamber, said shank being positioned within said chamber so as to be in alignment with the electrical connector within the handle probe for wiping engagement therewith whenever the handle probe is inserted into said housing chamber, said housing chamber being dimensioned for closely fitting non-rotatable insertion of said handle-probe therein so as to prevent rotation of said electro-surgical electrode during use and effectively isolate said shank and the receiving connector in the probe from the external surface of said handle and chuck.

2. A detachable chuck in accordance with claim 1 wherein the probe has at least one tab extending externally therefrom on a surface parallel to the axis of the elongated handle, said housing chamber having a recessed slot extending into one internal sidewall thereof dimensioned to receive the probe tab thereby snap-locking said housing onto the probe.

3. A detachable chuck in accordance with claim 1 which further includes at least one groove on the external surface of said housing with said groove extending generally perpendicular to said elongated conductor thereby facilitating gripping of said housing for attachment to and removal from the handle probe.

4. In an electro-surgical device, the combination comprising: a substantially flat electrically insulating handle having a main body with a narrow rectangular crosssection and a probe extending from one end of said main body and terminating in an extreme end surface wherein the probe likewise has a rectangular cross-section of reduced width and thickness relative to the main body, a port in the extreme end surface of the probe at least one electrical connector positioned within the probe parallel to the longitudinal axis thereof and in alignment with said port in the extreme end surface of the probe, said connector adapted to be connected in electrical communication with an electro-surgical generator through the handle, the probe including alignment tabs extending outwardly from the external surfaces of the probe, a housing composed of electrically insulating material having a cross-section at a first end thereof corresponding in external dimensions to the cross-section of the main body of the handle and having a chamber extending thereinto from said first end with internal dimensions corresponding to the external dimensions of the probe, said chamber receiving said probe and further having slots extending along the inner surfaces of said chamber receiving the tabs of said probe thereby effecting a releasable locking juncture, said housing having a conductor-receiving channel extending axially therethrough from said chamber to the opposite end of said housing, and an electrical conductor having an electrosurgical electrode end and a shank end, said conductor being sealed within said housing channel so that said shank extends into said chamber and axially entering the port in said probe to effect positive electrical communication with the connector in said probe by the wiping action between the probe connector and said shank, said electro-surgical electrode end of said conductor protruding externally from said housing from said opposite of said channel, said housing chamber being dimensioned for close fitting non-rotatable insertion of the handle probe therein for forming a locking mechanical support for said housing between the inner wall surfaces of said chamber and the external wall surfaces of said probe to isolate said handle port from the external environment.

5. In an electro-surgical device in accordance with claim 4 wherein the tabs on said probe are on the narrower alignment surfaces of the probe with a pair of externally raised ridges along the wider surfaces of the probe with each ridge parallel to the longitudinal axis of the probe, and ridge receiving groove means within said chamber for receiving respective ridges on said probe thereby guiding said probe into releasable locking engagement with said housing chamber.

6. In an electro-surgical device in accordance with claim 4 wherein said channel has a first collar at the interior wall of said chamber and a second axially spaced collar at the electrode end of said housing, said electrical conductor being sealably bonded to said first and second collars.

7. In an electro-surgical device in accordance with claim 4 wherein said probe has a plurality of electrical connectors therein, said housing having a plurality of said channels therethrough, said device further including a plurality of said conductors sealably retained within respective said channels.

* * * * *

UNITED STATES PATENT OFFICE
CERTIFICATE OF CORRECTION

Patent No. 4,014,343                    Dated 29 March 1977

Inventor(s) Janet M. Esty

It is certified that error appears in the above-identified patent and that said Letters Patent are hereby corrected as shown below:

Column 1, line 45, after "3,911,241" add -- , --.
         line 67, cancel "be" and substitute -- by --.

Column 3, line 34, after "of" cancel -- ; --.

Column 4, line 12, after "configuration" add -- . --.
         lines 31 and 32, cancel "profect" and substitute -- project --.

Column 5, line 1, after "chuck" add -- , --.
         line 26, cancel "chuch" and substitute -- chuck --.
         line 39, cancel "of" (1st occurrence) and substitute -- or --.

Column 6, line 2, cancel "electrosurgical" and substitute -- electro-surgical --.

UNITED STATES PATENT OFFICE
CERTIFICATE OF CORRECTION

Patent No. 4,014,343            Dated 29 March 1977

Inventor(s) Janet M. Esty

It is certified that error appears in the above-identified patent and that said Letters Patent are hereby corrected as shown below:

<u>Claim 1, Column 6,</u> line 46, cancel "handle-probe" and substitute -- handle probe --.

<u>Claim 4, Column 6,</u> line 67, cancel "corsssection" and substitute -- cross-section --.
         <u>Column 7,</u> line 26, cancel "electrosurgical" and substitute -- electro-surgical --.
         <u>Column 8,</u> line 3, after "opposite" add -- end --.

Signed and Sealed this

First Day of November 1977

[SEAL]

Attest:

RUTH C. MASON          LUTRELLE F. PARKER
*Attesting Officer*       *Acting Commissioner of Patents and Trademarks*